United States Patent
Han et al.

(10) Patent No.: US 9,248,165 B2
(45) Date of Patent: Feb. 2, 2016

(54) COMPOSITE CONTAINING COLLAGEN AND ELASTIN AS A DERMAL EXPANDER AND TISSUE FILLER

(75) Inventors: Bo Han, Temple City, CA (US); Marcel E. Nimni, Santa Monica, CA (US)

(73) Assignee: HANCOCK-JAFFE LABORATORIES, INC., Irvine, CA (US)

( * ) Notice: Subject to any disclaimer, the term of this patent is extended or adjusted under 35 U.S.C. 154(b) by 1217 days.

(21) Appl. No.: 13/127,275

(22) PCT Filed: Nov. 3, 2009

(86) PCT No.: PCT/US2009/063132
§ 371 (c)(1),
(2), (4) Date: Sep. 23, 2011

(87) PCT Pub. No.: WO2010/053918
PCT Pub. Date: May 14, 2010

(65) Prior Publication Data
US 2012/0010146 A1   Jan. 12, 2012

Related U.S. Application Data

(60) Provisional application No. 61/111,637, filed on Nov. 5, 2008.

(51) Int. Cl.
*A61K 38/39* (2006.01)
*A61K 8/64* (2006.01)
*A61Q 19/00* (2006.01)

(52) U.S. Cl.
CPC . *A61K 38/39* (2013.01); *A61K 8/64* (2013.01); *A61Q 19/00* (2013.01); *A61K 2800/91* (2013.01)

(58) Field of Classification Search
CPC .................................................... A61K 38/39
USPC .................. 514/18.8; 530/353, 356
See application file for complete search history.

(56) References Cited

U.S. PATENT DOCUMENTS

| | | | |
|---|---|---|---|
| 4,233,360 A | 11/1980 | Luck et al. | |
| 4,378,224 A | 3/1983 | Nimni et al. | |
| 4,424,208 A | 1/1984 | Wallace et al. | |
| 4,557,764 A | 12/1985 | Chu et al. | |
| 4,582,640 A | 4/1986 | Smestad et al. | |
| 4,760,131 A | 7/1988 | Sundsmo et al. | |
| 4,774,227 A | 9/1988 | Piez et al. | |
| 4,789,663 A | 12/1988 | Wallace et al. | |
| 4,803,075 A | 2/1989 | Wallace et al. | |
| 4,863,732 A | 9/1989 | Nathan et al. | |
| 4,950,483 A | 8/1990 | Ksander et al. | |
| 5,110,604 A | 5/1992 | Chu et al. | |
| 5,162,430 A | 11/1992 | Rhee et al. | |
| 5,219,576 A | 6/1993 | Chu et al. | |
| 5,304,595 A | 4/1994 | Rhee et al. | |
| 5,328,955 A | 7/1994 | Rhee et al. | |
| 5,374,539 A | 12/1994 | Nimni et al. | |
| 5,413,791 A | 5/1995 | Rhee et al. | |
| 5,446,091 A | 8/1995 | Rhee et al. | |
| 5,470,911 A | 11/1995 | Rhee et al. | |
| 5,475,052 A | 12/1995 | Rhee et al. | |
| 5,476,666 A | 12/1995 | Rhee et al. | |
| 5,510,418 A | 4/1996 | Rhee et al. | |
| 5,523,348 A | 6/1996 | Rhee et al. | |
| 5,527,856 A | 6/1996 | Rhee et al. | |
| 5,614,587 A | 3/1997 | Rhee et al. | |
| 5,643,464 A | 7/1997 | Rhee et al. | |
| 5,705,488 A | 1/1998 | Janzen et al. | |
| 2004/0162232 A1 | 8/2004 | Mitts et al. | |
| 2005/0142161 A1 | 6/2005 | Freeman et al. | |
| 2005/0209699 A1 | 9/2005 | Slivka et al. | |
| 2006/0073207 A1 | 4/2006 | Masters et al. | |
| 2006/0280769 A1 | 12/2006 | Chu et al. | |
| 2007/0003593 A1 | 1/2007 | Wironen et al. | |
| 2008/0038352 A1 | 2/2008 | Simpson et al. | |
| 2008/0064021 A1 | 3/2008 | Hedman et al. | |
| 2008/0096977 A1 | 4/2008 | Schankereli et al. | |
| 2008/0118947 A1 | 5/2008 | Yu et al. | |
| 2008/0175911 A1 | 7/2008 | McKay et al. | |
| 2009/0028817 A1* | 1/2009 | Niklason et al. | 424/85.2 |
| 2009/0209456 A1* | 8/2009 | Sweis | 514/9 |

OTHER PUBLICATIONS

L.L.H. Huang-Lee & M.E. Nimni, "Fibroblast Contraction of Collagen Matrices With and Without Hyaluronan," J Biomater. Sci. Polymer Ed. 5: 99-109 (1993).

F. P. Luyten et al., "Purification and Partial Amino Acid Sequence of Osteogenin, a Protein Initiating Bone Differentiation," J. Biol. Chem. 264: 13377-13380 (1989).

E. Öäzkaynak et al., "Murine Osteogenic Protein (OP-1): High Levels of mRNA in Kidney," Biochem. Biophvs. Res. Commun. 179: 116-123 (1991).

R. M. Harland et al., "The Transforming Growth Factor Family and Induction of the Vertebrate Mesoderm: Bone Morphogenetic Proteins are Ventral Inducers," Proc. Natl. Acad. Sci. USA 91: 10243-10246 (1994).

(Continued)

*Primary Examiner* — David Lukton

(74) *Attorney, Agent, or Firm* — Ditthavong & Steiner, P.C.

(57) ABSTRACT

An injectable composition having dermal filling and tissue expanding activity comprises (1) a quantity of elastin sufficient to bring about dermal filling and tissue expansion when injected into a subject in need of dermal filling and tissue expansion, and (2) a pharmaceutically acceptable carrier. The composition can further comprise collagen, in other alternatives, the composition can further comprise hyaluronic acid, and one or more of the elastin, the collagen, and the hyaluronic acid, if present can be cross-linked, either intramolecularly or intermolecularly. The elastin, however, is the primary filler, even if collagen or hyaluronic acid are included in the composition.

4 Claims, 11 Drawing Sheets

(56) References Cited

OTHER PUBLICATIONS

C. Scheufler et al., "Crystal Structure of Human Bone Morphogenetic Protein-2 at 2.7 Å Resolution," J. Mol. Biol. 287: 103-115 (1999).
J. Q. Feng et al., "Structure and Sequence of Mouse Bone Morphogenetic Protein-2 Gene (BMP-2): Comparison of the Structures and Promoter Regions of BMP-2 and BMP-4 Genes" Biochim. Biophys. Acta 1218: 221-224 (1994).
B. L. Rosenzweig et al., "Cloning and Characterization of a Human Type II Receptor for Bone Morphogenetic Proteins," Proc. Natl. Acad. Sci. USA 92: 7632-7636 (1995).
M. Kawabata et al., "Signal Transduction by Bone Morphogenetic Proteins," Cytokine Growth Factor Rev. 9: 49-61 (1998).
B. Han et al., "Proanthocyanidin: A Natural Crosslinking Reagent for Stabilizing Collagen Matrices," J. Biomed. Mater. Res. 65A: 118-124 (2003).

\* cited by examiner

Elastin with gelatin as carrier, 4w

Elastin crosslink with expoxid and gelatin as carrier x200

Elastin crosslinked with PA, gelatin as carrier

HA crosslinked to DBM surface, 23G needle x40

HA crosslinked to DBM surface, 23G needle x200

DBM crosslinked with PA x200

1. Crosslink elastin with proanthocyanidin (PA), epoxide (EP) and hyaluronic acid (HA) and subcutaneous implantation in rats for 4 weeks.

Elastin groups:
- Mild foreign tissue responses in all groups
- Strong tissue regeneration around implants
- Overall degradation rates in elastin groups are low.
- PA and HA appears induce more fibroblast cells infiltration into elastin particles.
- Regenerations are obvious surround the elastin particles and into the fiber spaces

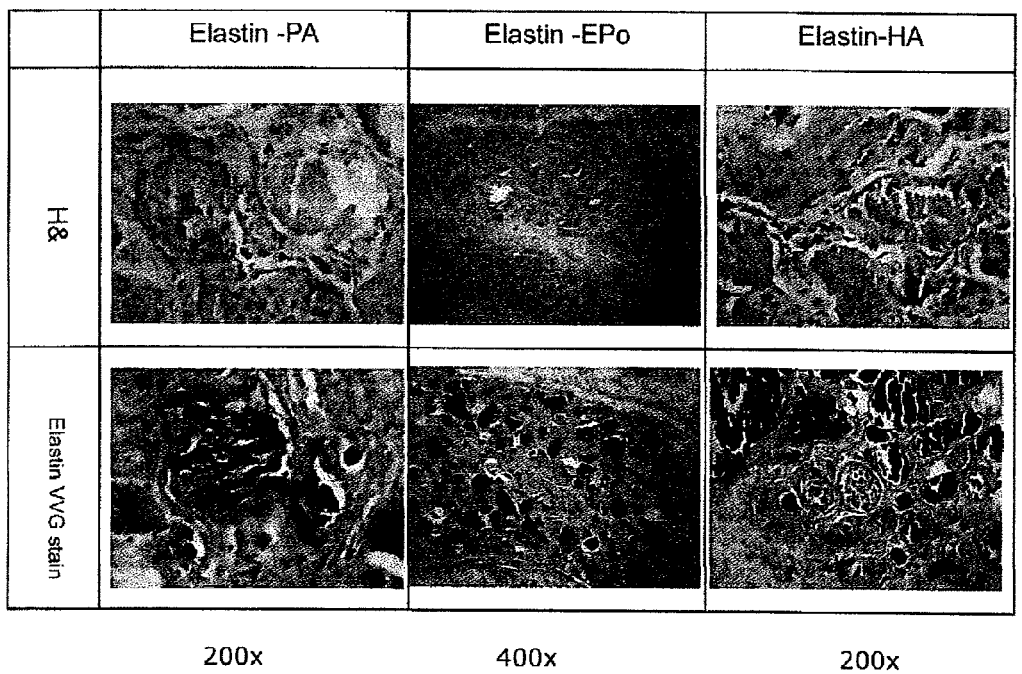

Fig. 7

Implants kept the injected shapes throughout the implantation period.
No or little contracture bands (4w), x100
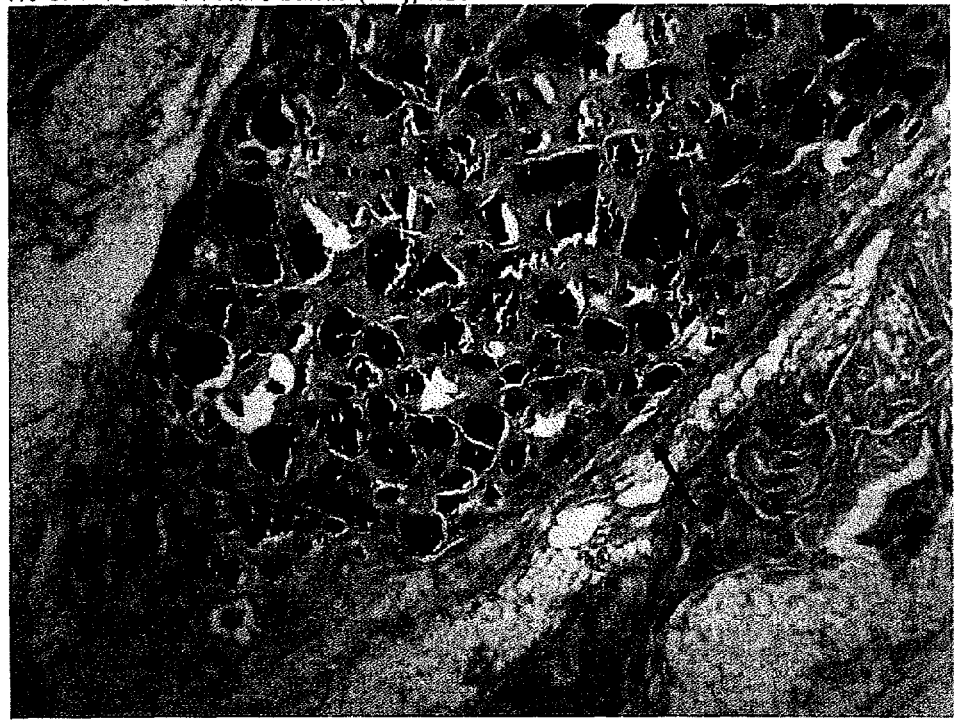
A.
B.
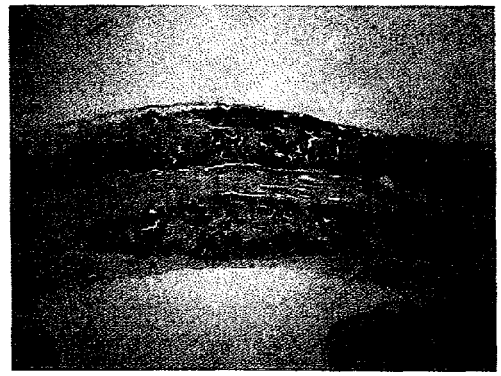
C.
Fig. 8

Fibrous tissues formed surround the elastin particles (solid arrow) and fibroblast migrated into elastin fiber to regenerate fibrous tissues (dotted arrows). X200

2. Insoluble collagen with elastin and different implantation time:

Elastin + Collagen, 8 weeks, rat subcutaneous

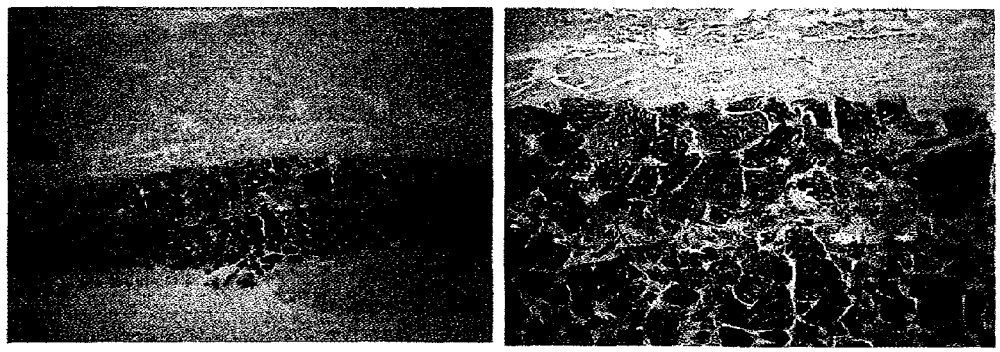
FIG. 10D
 
FIG. 11A          FIG. 11B

COMPOSITE CONTAINING COLLAGEN AND ELASTIN AS A DERMAL EXPANDER AND TISSUE FILLER

CROSS-REFERENCES

This application is a national stage entry of PCT/US09/63132, filed Nov. 3, 2009, which claims priority from U.S. Provisional Application Ser. No. 61/111,637 by Han et al., entitled "Composite Containing Collagen, Elastin, and Hyaluronic Acid as a Dermal Expander and Tissue Filler" and filed on Nov. 5, 2008, the contents of which are hereby incorporated herein in their entirety by this reference.

FIELD OF THE INVENTION

This invention is directed to a composition for injection that acts as a dermal expander and tissue filler. The composition is a composite that contains collagen, elastin, and hyaluronic acid; the collagen, elastin, and hyaluronic acid can be covalently cross-linked; in particular, the elastin is cross-linked or otherwise stabilized by interaction with a proanthocyanidin.

BACKGROUND OF THE INVENTION

As the skin ages, many people experience dissatisfaction in their appearance due to the development of lines and wrinkles in the skin, especially the face. Although the development of these lines and wrinkles is generally seen as a part of the natural aging process, for many individuals, the appearance of these lines and wrinkles is very traumatic and seriously affects their quality of life and their relationships with others. In addition, for a large number of people, the appearance of aging can affect their economic prospects. This is especially true for those seeking employment as actors or actresses or in other positions in the entertainment industry, but there is an increasing concern among an aging population that an aged appearance can affect their job prospects, even for jobs for which appearance is essentially unrelated to job performance.

Therefore, as a result of these concerns, there is a substantial need for products that can reverse some of the effects of the aging process and can act as dermal expanders and tissue fillers. Accordingly, a number of compositions are in use as dermal expanders and tissue fillers. Some of these are collagen-based. One alternative uses atelopeptide collagen alone, such as Zyderm (from bovine collagen), or micronized human collagen from cadavers. Another alternative uses cross-linked collagen, such as Zyplast, which uses bovine collagen cross-linked by glutaraldehyde, or Evolence, which uses porcine collagen cross-linked by ribose. Other compositions in use as dermal expanders and tissue fillers are hyaluronic acid-based, either native or cross-linked. These dermal expanders and tissue fillers have several problems. They have a great tendency to be resorbed, require repeated injections, and there is a risk of toxicity from the cross-linking agents used.

Another approach uses composites. These include, for example, CaHA microspheres suspended in a gel carrier (Radiesse), PMMA beads suspended in gelatin (ArteFill), PLA beads, TCP powder, or dextran beads in hyaluronic acid (HA). These composites also have several problems. For example, the beads used are non-biological and tend to migrate, which causes distortion of the appearance of the skin.

There are additional uses for dermal expanders and tissue fillers that require dermal expanders or skin fillers with improved properties. These are in breast augmentation, treatment for urinary incontinence, or treatment for esophageal reflux. Such dermal expanders and fillers can be employed in other surgical reconstructive processes. Such dermal expanders and fillers can also be employed in dental implants, where they can aid in bone regeneration.

Accordingly, there is a need for an improved dermal expander and tissue filler that is effective, safe, and whose effects are lasting. There is also a need for an improved dermal expander and tissue filler that can be employed in non-cosmetic applications such as breast augmentation, treatment for urinary incontinence, or treatment for esophageal reflux.

SUMMARY OF THE INVENTION

The present invention describes improved dermal expanders and tissue fillers that meet the needs described above.

Injectable implant compositions for soft tissue augmentation comprise collagen (obtained from skin, tendon or bone) and elastin (obtained from arteries or tendons and ligaments). The elastin is the primary filler. The compositions are suspended in a physiological saline solution for intradermal injection or other soft tissue augmentation. The composite in question is retained at the site of injection for prolonged periods of time for the purpose of eliminating wrinkles or other visible surface imperfections in the skin. Other ingredients can be included, such as, but not limited to, hyaluronic acid.

Since the 1980's injectable collagen, usually from bovine sources, but most recently also of human origin, has been used as at tissue filler to eliminate wrinkles and other facial imperfections, usually associated with the aging process. In recent years other natural, synthetic and inert fillers have been used for the same purpose. Presently the use of these alternate materials exceeds that of bovine collagen, which is being replaced by materials which are more lasting and have a lesser tendency to be reactive and induce allergic reactions. Hyaluronic acid and its derivatives, principally cross-linked hyaluronic acid, are gaining more and more acceptance and are becoming the most widely used tissue fillers. Among these, non animal derived hyaluronic acid is receiving the greatest acceptance because of the very small incidence of allergic reactions and the almost immediate ability to correct facial wrinkles or folds. Most of these acceptable currently used fillers will retain satisfactory beneficial results for periods longer than 6 months and up to 1 year, at which time application has to be repeated.

Elastin is an important skin component which contributes to the natural properties of skin, and it is one of the dermal components which more readily becomes depleted during the process of aging. Because of the nature of its chemical composition, and the uniqueness of its cross-linking network, which contributes to make it one of the most insoluble proteins in the body, it is very resistant to chemical and enzymatic degradation. Nevertheless UV light has the tendency to destroy the complex cross-links, opening the ring structure of pyridine groups which stabilize the protein structure. Sun light exposure is known to induce a phenomenon, described as solar elastosis, which causes degradation and loss of structure of skin elastin and alters the properties of collagen. The phenomenon is very well described and has been studied extensively in the weathered skin of individuals who are constantly exposed to sunlight and consequent to sun induced skin damage. In some alternatives, proanthocyanidin is added, which, because of its antioxidant properties, is expected to further protect the injected elastin from UV degradation. When elastin is used, it is highly preferred to cross-link the elastin with a proanthocyanidin. Preferably, a proanthocyanidin is used at a concentration of from about 0.1% to about 1.0%. The pH is preferably from about 7.0 to about 8.5. The interaction of the proanthocyanidin can be described as stabilizing, cross-linking, or coating. The use of a proanthocyanidin to cross-link, stabilize, or coat elastin in a microparticle suspension is highly preferred in order to prevent its biodegradation. If not cross-linked, stabilized, or coated, elastin degrades rapidly, as determined by an in vitro enzyme degradation test.

In the present invention we have combined collagen and elastin in the formulation. The natural resistance of elastin to degradation, coupled with its space filling ability when combined with collagen satisfies the criteria of ideal filler. It contains all the natural materials present in the dermis to achieve the ultimate goal of retaining a smooth outer appearance of the skin by eliminating the empty spaces and reversing the contractile process that is responsible for the superficial uneven appearance of skin. In some alternatives, a glycosaminoglycan such as hyaluronic acid can be included as well; in such alternatives, the collagen and the hyaluronic acid can form a collagen-hyaluronan complex.

The present invention contains a mixture of collagen, elastin, and the glycosaminoglycan or any of their combinations.

Collagen can be in its native form, in a denatured form (gelatin) or cross-linked endogenously or exogenously.

Collagen can be obtained from a variety of animal and human tissues, such as skin, tendon, ligament, pericardium, dural membrane, small intestine mucosa, and bone, as well as other tissues.

Elastin can be obtained from animal and human tendon, such as bovine ligamentum nuchae, aorta roots, blood vessels, pericardium, as well as other tissues.

Accordingly, one aspect of the invention is an injectable composition having dermal filling and tissue expanding activity comprising:

(1) a quantity of elastin sufficient to bring about dermal filling and tissue expansion when injected into a subject in need of dermal filling and tissue expansion; and (2) a pharmaceutically acceptable carrier.

Typically, the elastin is selected from the group consisting of non-human mammalian elastin and human elastin. If the elastin is non-human mammalian elastin, it is typically porcine elastin.

The pharmaceutically acceptable carrier can comprise gelatin. It can further comprise phosphate buffered saline or other excipients; other excipients such as glucose or maltose have been described and are known in the art. In another alternative, the pharmaceutically acceptable carrier can comprise carboxymethylcellulose. Other acceptable carriers are known in the art.

In one preferred alternative, the composition further comprises a rapid-acting local anesthetic. The rapid-acting local anesthetic can be selected from the group consisting of lidocaine, benzocaine, tetracaine, bupivacaine, cocaine, etidocaine, flecainide, mepivacaine, pramoxine, prilocaine, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Typically, the rapid-acting local anesthetic is lidocaine.

The elastin can be cross-linked with a cross-linking agent. The cross-linking agent can be selected from the group consisting of a proanthocyanidin, a bifunctional epoxide, a carbodiimide, glutaraldehyde, and periodate. If the cross-linking agent is a proanthocyanidin, it is typically selected from the group consisting of proanthocyanidin, procyanidin (2H-1-benzopyran-3,4,5,7-tetrol, 2-(3,4-dihydroxyphenyl)-2-((2-(3,4-dihydroxyphenyl)-3,4-dihydro-5,7-dihydroxy-2H-1-benzopyran-3-yl)oxy)-3,4-dihydro), procyanidin B, procyanidin B2, rhatannin, procyanidol oligomer, procyanidin C, procyanidin B3, procyanidin B1, selligueain A (8,14-methano-2H,14H-1-benzopyrano(7,8-d)(1,3)benzodioxocin-3,5,11,13,15-pentol, 4-(3,4-dihydro-3,5,7-trihydroxy-2-(4-hydroxyphenyl)-2H-1-benzopyran-8-yl)-3,4-dihydro-2,8-bis(4-hydroxyphenyl)-, (2R-(2α,3α,4β(2R*,3S*),8β,14β,15R*)), geranin A, geranin D, procyanidin B5, procyanidin B5-3'-O-gallate, vitisinol, amurensisin, terminalin, geranin B, 6,8-dihydroxyafzelin, afzelin-3"-O-gallate, geranin C, afzelin, flavangenol, carallidin, mahuannin A, proanthocyanidin A1, proanthocyanidin A2, procyanidin D, and analogues, derivatives, and bioisosteres of these compounds. Preferably, a proanthocyanidin is used at a concentration of from about 0.1% to about 1.0%. The pH is preferably from about 7.0 to about 8.5. The interaction of the proanthocyanidin can be described as stabilizing, cross-linking, or coating. In most embodiments of the invention, it is highly preferred to use a proanthocyanidin as a cross-linking agent. However, other cross-linking agents can be used. If the cross-linking agent is a bifunctional epoxide, it is typically 1,4-butanediol diglycidyl ether. If the cross-linking agent is a carbodiimide, the carbodiimide is typically selected from the group consisting of 1-ethyl-3-(3-dimethylaminopropyl) carbodiimide hydrochloride (EDC), dicyclohexylcarbodiimide (DCC), 1-ethyl-3-(4-azonia-4,4-dimethylpentyl) carbodiimide iodide (EAC); 1-cyclohexyl-3-(2-morpholinyl-(4)-ethyl-carbodiimide metho-p-toluenesulfonate (CMC), and N-benzyl-N'-3-dimethylaminopropyl-carbodiimide hydrochloride (BDC). Preferably, the carbodiimide is 1-ethyl-3-(3-dimethylaminopropyl) carbodiimide hydrochloride (EDC).

In one preferred alternative, the elastin is cross-linked with a glycosaminoglycan. The glycosaminoglycan can be selected from the group consisting of hyaluronic acid, chondroitin sulfate, pentosan polysulfate, dermatan sulfates, heparin, heparan sulfates, and keratan sulfates. Typically, the glycosaminoglycan is hyaluronic acid. Suitable cross-linking agents are as described above. When the glycosaminoglycan is hyaluronic acid, the hyaluronic acid can be obtained from rooster combs or can be synthesized by bacteria.

In another preferred alternative, the composition further comprises collagen. The collagen can be native or denatured collagen obtained from skin, tendon, ligament, pericardium, dural membrane, small intestine mucosa or bone. The collagen can be used in soluble form, fibrillar form, a form of an insoluble slurry, or hydrogel form. The collagen can be human Type I collagen. The human Type I collagen can be obtained from demineralized bone matrix (DBM). Alternatively, the collagen can be collagen from porcine tendon. The collagen can be cross-linked intramolecularly. Suitable cross-linking agents are described above. Alternatively, the collagen can be cross-linked to the elastin, or the collagen can be cross-linked to a glycosaminoglycan such as, but not limited to, hyaluronic acid, which can also be included in the composition in that alternative.

The elastin can be obtained from human or animal ligaments or arteries. Typically, the elastin is purified from non-elastineous proteins and proteoglycans. Typically, the elastin is cryofractured into a fine particle. Preferably, the size of the fine particle is from about 50 μm to about 210 μm. Typically, the elastin concentration is from about 20 mg/mL to about 300 mg/mL; preferably, the elastin concentration is from about 20 mg/mL to about 100 mg/mL.

In one alternative of this aspect of the invention, the composition further comprises collagen and a glycosaminoglycan such as, but not limited to, hyaluronic acid, and wherein one or more of the elastin, the collagen, and the glycosaminoglycan are cross-linked, either intramolecularly or intermolecularly. Suitable cross-linking agents are described above.

Another aspect of the invention is a method of dermal filling and tissue expansion comprising the step of injecting a quantity of this embodiment of a composition according to the present invention as described above sufficient to induce dermal filling and tissue expansion to a patient in need thereof. In this method, the dosage, the frequency of the dosage, and the route of injection can be chosen by a skilled clinician taking into account factors known in the art and described in detail further below.

Another aspect of the present invention is an injectable composition having dermal filling and tissue expanding activity comprising:

(1) an insoluble collagen suspension in a quantity sufficient to bring about dermal filling and tissue expansion when injected into a subject in need of dermal filling and tissue expansion; and (2) a pharmaceutically acceptable carrier.

Typically, in this composition, the concentration of collagen is from about 20 mg/mL to about 100 mg/mL. Typically, in this composition, the collagen is cross-linked with a cross-linking agent, as described above.

Typically, in this composition, the pharmaceutically acceptable carrier is gelatin.

In this aspect of the invention, the composition can further comprise elastin. In one preferred alternative when the composition comprises elastin, the composition comprises 75 mg of elastin particles and 25 mg of insoluble collagen per 1.0 mL of pharmaceutically acceptable carrier. In this alternative, the pharmaceutically acceptable carrier can be gelatin.

In this aspect of the invention, the collagen can be partially denatured into gelatin to aid in maintaining the components in suspension and in facilitating the injection of the mixture through a narrow gauge needle.

Another aspect of the invention is a method of dermal filling and tissue expansion comprising the step of injecting a quantity of this embodiment of a composition according to the present invention as described above sufficient to induce dermal filling and tissue expansion to a patient in need thereof. In this method, the dosage, the frequency of the dosage, and the route of injection can be chosen by a skilled clinician taking into account the factors described further in detail below.

Yet another aspect of the present invention is a method for augmenting the volume area of dermal tissue at sites where wrinkles and other tissue imperfections have caused visible changes associated with loss or rearrangement of the subcutaneous collagen network comprising the step of: providing an effective amount of a composition, which can be injected locally, and which consists of a mixture of macromolecules which are native constituents of the skin, the mixture comprising collagen, elastin and, optionally, a glycosaminoglycan, such as, but not limited to, hyaluronic acid, which are held together by covalent, ionic or hydrogen bonds, and which include natural materials which have been demonstrated to increase the natural synthesis of these molecules by cells which reside in the dermis. In this method, the collagen can be native or denatured collagen obtained from skin, tendon, ligament, pericardium, dural membrane, small intestine mucosa or bone. The collagen can be used in soluble form, fibrillar form, a form of an insoluble slurry, or hydrogel form. The collagen can be cross-linked intramolecularly. Alternatively, the collagen can be cross-linked to the elastin or to the glycosaminoglycan, such as, but not limited to, hyaluronic acid. The collagen can be insoluble collagen; when the collagen is insoluble collagen, the concentration of insoluble collagen is typically from about 20 mg/mL to about 100 mg/mL.

The elastin used can be obtained from human or animal ligaments or arteries. The elastin is typically purified from non-elastineous proteins and proteoglycans. The elastin is typically cryofractured into a fine particle. Typically, the size of the fine particle is from about 50 μm to about 210 μm.

In this method, the injectable composition used typically comprises gelatin.

In this method, typically, the elastin concentration is from about 20 mg/mL to about 100 mg/mL.

In this method, when the glycosaminoglycan is hyaluronic acid, the hyaluronic acid used can be obtained from rooster combs or is synthesized by bacteria.

In this method, at least one of the collagen, the elastin, and, if present, the glycosaminoglycan, such as, but not limited to, hyaluronic acid, can be cross-linked, either intramolecularly or intermolecularly, by use of a cross-linking agent. The cross-linking agent can be selected from the group consisting of proanthocyanidin, a bifunctional epoxide, a carbodiimide, and glutaraldehyde, as described above. As another alternative, collagen or gelatin can be cross-linked to hyaluronic acid, as described in L. L. H. Huang-Lee & M. E. Nimni, "Fibroblast Contraction of Collagen Matrices With and Without Covalently Bound Hyaluronan," *J. Biomater. Sci. Polymer Ed.* 5: 99-109 (1993), incorporated herein by this reference. As yet another alternative, additional stabilizing cross-links can be introduced into at least one of the collagen, the elastin, and the glycosaminoglycan, by use of a water-soluble carbodiimide, a periodate, or an epoxide.

Typically, in this method, the mixture is dried, pulverized into small particles, suspended in a physiological compatible solution, and injected subcutaneously or intradermally to humans.

BRIEF DESCRIPTION OF THE DRAWINGS

These and other features, aspects, and advantages of the present invention will become better understood with reference to the following description, appended claims, and accompanying drawings where:

FIG. 7 shows the results of elastin cross-linked with proanthocyanidin (PA), epoxide (EP), or hyaluronic acid (HA) with subcutaneous implantation in rats for four weeks. The results are shown in FIG. 7 in the following arrangement. The leftmost column is elastin cross-linked with PA, the center column is elastin cross-linked with EP, and the rightmost column is EP cross-linked with HA. The top row shows staining with hematoxylin-eosin (H & E); the bottom row shows staining with Verhoeff-Van Gieson stain (VVG), which stains elastic fibers (in black) and collagen (in red). In the results of FIG. 7, the elastin groups showed mild foreign tissue responses in all groups. They showed strong tissue regeneration around implants. The overall degradation rates in elastin groups were low. PA and HA appear to induce more infiltration of fibroblast cells into elastin particles. Regeneration is obvious surrounding the elastin particles and into the fiber spaces. In FIG. 7, elastin-PA and elastin-HA are shown at 200× magnification; elastin-EP is shown at 400× magnification.

FIG. 8 shows that the implants kept their injected shapes throughout the implantation period. Few or no contracture bands are seen in FIG. 8 (100× magnification, 4-week implantation, panels A-C).

FIG. 10 shows the results of implantation of insoluble collagen together with elastin, elastin cross-linked with proanthocyanidin, or elastin alone, using different implantation times and routes of implantation. FIG. 10D shows elastin cross-linked with hyaluronic acid implanted intracutaneously in rats for 6 weeks (left and right panels).

FIG. 11 shows the results with mixtures of collagen and elastin. FIG. 11A shows the results with 75% collagen and 25% elastin implanted subcutaneously in rats for 4 weeks. FIG. 11B shows the results with 25% collagen and 75% elastin implanted subcutaneously in rats for 4 weeks.

DETAILED DESCRIPTION OF THE INVENTION

Figure 1:
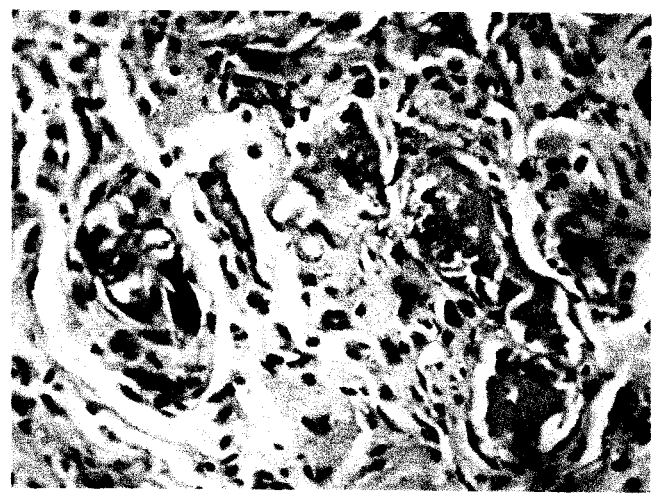
FIG. 1 is a photomicrograph at ×200 magnification showing the results with elastin (without cross-linking) with gelatin as a carrier after four weeks in rats treated with the composition (Example 4).

Injectable implant compositions for soft tissue augmentation according to the present invention comprise collagen (obtained from skin, tendon or bone) and elastin (obtained from arteries or tendon and ligament). The elastin is the primary filler and is the most important ingredient in achieving the desired soft tissue augmentation effect. Typically the composition is suspended in a physiological saline solution for intradermal injection or other soft tissue augmentation. The composite in question is retained at the site of injection for prolonged periods of time for the purpose of eliminating wrinkles or other visible surface imperfections in the skin. Compositions according to the present invention can further comprise other ingredients, such as a glycosaminoglycan such as hyaluronic acid. If hyaluronic acid is included in the composition, the collagen and hyaluronic acid can form a collagen-hyaluronan complex.

Since the 1980's injectable collagen, usually from bovine sources, but most recently also of human origin, has been used as at tissue filler to eliminate wrinkles and other facial imperfections, usually associated with the aging process. In recent years other natural, synthetic and inert fillers have been used for the same purpose. Presently the use of these alternate materials exceeds that of bovine collagen, which is being replaced by materials which are more lasting and have a lesser tendency to be reactive and induce allergic reactions. Hyaluronic acid and its derivatives, principally cross-linked hyaluronic acid, are gaining more and more acceptance and are becoming the most widely used tissue fillers. Among these, non animal derived hyaluronic acid is receiving the greatest acceptance because of the very small incidence of allergic reactions and the almost immediate ability to correct facial wrinkles or folds. Most of these acceptable currently used fillers will retain satisfactory beneficial results for periods longer than 6 months and up to 1 year, at which time application has to be repeated.

Elastin is an important skin component which contributes to the natural properties of skin, and it is one of the dermal components which more readily becomes depleted during the process of aging. Because of the nature of its chemical composition, and the uniqueness of its cross-linking network, which contributes to make it one of the most insoluble proteins in the body, it is very resistant to chemical and enzymatic degradation. Nevertheless UV light has the tendency to destroy the complex cross-links, opening the ring structure of pyridine groups which stabilize the protein structure. Sunlight exposure is known to induce a phenomenon, described as solar elastosis, which causes degradation and loss of structure of skin elastin and alters the properties of collagen. The phenomenon is very well described and has been studied extensively in the weathered skin of individuals who are constantly exposed to sunlight and consequent to sun induced skin damage.

In the present invention we have combined collagen and elastin in the formulation; optionally, a glycosaminoglycan such as hyaluronic acid can be further included. The natural resistance of elastin to degradation, coupled with its space filling ability, when combined with collagen or a collagen-hyaluronan complex (if hyaluronic acid is present) satisfies the criteria of ideal filler. The elastin is the primary filler. It contains all the natural materials present in the dermis to achieve the ultimate goal of retaining a smooth outer appearance of the skin by eliminating the empty spaces and reversing the contractile process that is responsible for the superficial uneven appearance of skin.

The present invention contains a mixture of collagen, elastin and, optionally, a glycosaminoglycan such as hyaluronic acid, or any of their combinations.

Collagen is a fibrous protein with a triple helical structure. A single molecule of Type I collagen is comprised of three polypeptide chains with an aggregate molecular mass of ~285 kDa. The molecule has a rodlike shape with a length of ~3000 Å and a width of ~14 Å. Collagen has an extremely distinctive amino acid composition; nearly one-third of its amino acid residues are glycine; another 15% to 30% are proline or 4-hydroxyproline (Hyp) residues, with a smaller number of 3-hydroxyproline and 5-hydroxylysine residues. These hydroxylated amino acid residues, which are formed as the result of posttranslational modification, confer stability on collagen, probably through intramolecular hydrogen bonds involving bridging water molecules. Collagen contains many repeated iterations of the sequence Gly-X—Y, where X is often proline and Y is often 4-hydroxyproline. This forms a triple helical structure. Collagen is organized into fibrils. Collagen contains covalently attached carbohydrates in amounts that range from ~0.4% to 12% by weight. The carbohydrates consist mostly of glucose, galactose, and disaccharides, and are covalently attached to collagen at the 5-hydroxylysine residues. Collagen fibrils are also covalently cross-linked through reactions involving lysine and histidine residues.

Elastin is another fibrous protein, one which, in its native form, has elastic, rubber-like properties. Elastin is primarily composed of the amino acids glycine, valine, alanine, and proline. It is a specialized protein with a molecular mass of 64 to 66 kDa. It has an irregular or random coil conformation made up of 830 amino acids. Elastin is made by linking many soluble tropoelastin protein molecules, in a reaction catalyzed by lysyl oxidase, to make a massive, insoluble, durable array that is cross-linked. The amino acid responsible for these cross-links is lysine. The non-standard amino acids desmosine and isodesmosine are both found in elastin.

Collagen can be native form, denatured form (gelatin) or cross-linked endogenously or exogenously.

Collagen can be obtained from a variety of animal and human tissues, such as, but not limited to, skin, tendon, ligament, pericardium, dural membrane, small intestine mucosa, or bone. In one preferred alternative, collagen is purified from porcine tendon.

Elastin can be obtained from animal and human tendon, such as, but not limited to, bovine ligamentum nuchae, aorta roots, blood vessels, or pericardium. In one preferred alternative, elastin is purified from porcine aorta root.

In another preferred alternative, collagen is purified from human bone. Collagen derived from human bone is readily available as a discard from bone banks which manufacture DBM (demineralized bone matrix), used primarily as a filler for defects where bone is lost or is insufficient for adequate repair following surgical procedures (spinal fusion, prosthetic implants, or other procedures).

The DBM which is usually discarded is poor in bone inducing growth factors but still retains some biological activity which can enhance soft tissue regeneration. The biological activity of this material, in terms of its ability to stimulate fibroblasts to make new collagen at the site of the implant may further contribute to the efficacy and durability of the implant by stimulating the local cells of the dermis to make more collagen, therefore supplementing the filling effect of the injected composite.

Animal studies attached clearly demonstrate the retention of the collagen-hyaluronic acid-elastin mixture after a prolonged period of implantation. Other composites, not cross-linked or without elastin, do not display similar properties which reflect the ability to be retained and act efficiently as fillers.

Elastin is obtained from tendons/ligaments of human or animal origin. It is prepared by sequentially extracting proteoglycans and collagen from the dissected tissues. (R J Boucek, in Collagen, CRC Press, Editor M. Nimni, vol III, p201 (1985). The residue after this process is autoclaved and the insoluble residue consists of pure elastin. It is pulverized for future use.

Collagen and hyaluronic acid are covalently cross-linked using standard cross-linking reagents and procedures (Nimni et al Matrix Biology (1994) 14 147-157), U.S. Pat. Nos. 4,378,224 and 5,374,539 to Nimni). Other cross-linking agents are known in the art and are described below. With regard to cross-linking, the term "intramolecularly" and similar terminology refer to cross-links between the same type of molecule, such as elastin cross-linked to elastin. The cross-links need not involve the same molecule, although this is possible. With regard to cross-linking, the term "intermolecularly" and similar terminology refer to cross-links between different types of molecules, such as elastin being cross-linked to collagen or hyaluronic acid or collagen being cross-linked to hyaluronic acid.

The collagen-HA composite is now suspended in saline together with the pulverized elastin. A rapid-acting local anesthetic is added to eliminate any possible pain associated with the subcutaneous injection of the suspension. A suitable rapid-acting local anesthetic is lidocaine; alternatively, other analogous local anesthetics such as benzocaine, tetracaine, bupivacaine, cocaine, etidocaine, flecainide, mepivacaine, pramoxine, prilocaine, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, or pharmaceutically acceptable derivatives and bioisosteres thereof can be used. When the rapid-acting local anesthetic is lidocaine, a suitable concentration of lidocaine is 0.3%.

Suitable cross-linking reagents and methods include the following: (1) the bioflavonoid proanthocyanidin, a natural cross-linking agent, at 0.05% concentration; (2) a bifunctional epoxide such as 1,4-butanediol diglycidyl ether; (3) a carbodiimide, such as, but not limited to 1-ethyl-3-(3-dimethylaminopropyl) carbodiimide hydrochloride (EDC), and (4) glutaraldehyde. As used herein, the terms "a proanthocyanidin" or "proanthocyanidins" includes all proanthocyanidins and their analogues as further described in detail below.

Proanthocyanidins are dimers and oligomers of flavan-3-ol units (catechin analogues) linked mainly through C4 to C8 bonds to leucoanthocyanidins. Proanthocyanidins include, but are not limited to, proanthocyanidin, procyanidin (2H-1-benzopyran-3,4,5,7-tetrol, 2-(3,4-dihydroxyphenyl)-2-((2-(3,4-dihydroxyphenyl)-3,4-dihydro-5,7-dihydroxy-2H-1-benzopyran-3-yl)oxy)-3,4-dihydro), procyanidin B, procyanidin B2, rhatannin, procyanidol oligomer, procyanidin C, procyanidin B3, procyanidin B1, selligueain A (8,14-methano-2H,14H-1-benzopyrano(7,8-d)(1,3)benzodioxocin-3,5,11,13,15-pentol, 4-(3,4-dihydro-3,5,7-trihydroxy-2-(4-hydroxyphenyl)-2H-1-benzopyran-8-yl)-3,4-dihydro-2, 8-bis(4-hydroxyphenyl)-,(2R-(2α,3α,4β(2R*,3S*),8β,14β, 15R*)), geranin A, geranin D, procyanidin B5, procyanidin B5-3'-O-gallate, vitisinol, amurensisin, terminalin, geranin B, 6,8-dihydroxyafzelin, afzelin-3"-O-gallate, geranin C, afzelin, flavangenol, carallidin, mahuannin A, proanthocyanidin A1, proanthocyanidin A2, procyanidin D, and analogues, derivatives, and bioisosteres of these compounds.

As described further below, it is highly preferred to cross-link the elastin with a proanthocyanidin. Preferably, a proanthocyanidin is used at a concentration of from about 0.01% to about 1.0%; more preferably, the proanthocyanidin is used at a concentration of from about 0.1% to about 1.0%. The pH is preferably from about 5.5 to about 8.4; more preferably, the pH is from about 7.8 to about 8.4. The interaction of the proanthocyanidin can be described as stabilizing, cross-linking, or coating. The use of a proanthocyanidin to cross-link, stabilize, or coat elastin in a microparticle suspension is highly preferred in order to prevent its biodegradation. If not cross-linked, stabilized, or coated, elastin degrades rapidly, as determined by an in vitro enzyme degradation test.

Other carbodiimides are known in the art, including, but not limited to dicyclohexylcarbodiimide (DCC), 1-ethyl-3-(4-azonia-4,4-dimethylpentyl) carbodiimide iodide (EAC); 1-cyclohexyl-3-(2-morpholinyl-(4)-ethyl-carbodiimide metho-p-toluenesulfonate (CMC), and N-benzyl-N'-3-dimethylaminopropyl-carbodiimide hydrochloride (BDC). These and other suitable cross-linking reagents and procedures are described in S. S. Wong, "Chemistry of Protein Conjugation and Cross-linking" (CRC Press, Boca Raton, Fla., 1993), the contents of which are incorporated herein by this reference. Still other suitable cross-linking agents can be used, such as the difunctionally activated polyethylene glycols described in U.S. Pat. No. 5,643,464 to Rhee et al., incorporated herein by this reference.

Figure 5:
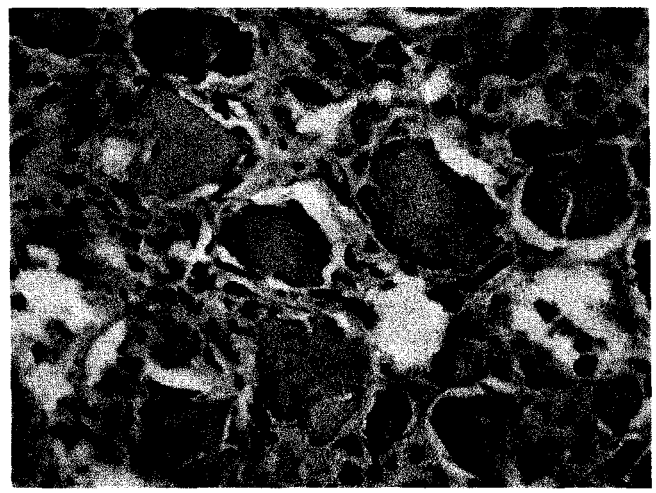
FIG. 5 is another photomicrograph at ×200 magnification showing the results with hyaluronic acid cross-linked to a DBM surface, injected with a 23 G needle in rats treated with the composition (Example 4).

Another cross-linking method is oxidative cross-linking with periodate. When periodate is used as a cross-linker, the aldehydes formed can then be stabilized further by reaction with sodium borohydride or sodium cyanoborohydride to give rise to more permanent cross-links, such as collagen-hyaluronic acid cross-links, as shown in FIG. 5 of L. L. H. Huang-Lee & M. E. Nimni, "Fibroblast Contraction of Collagen Matrices With and Without Covalently Bound Hyaluronan," *J. Biomater. Sci. Polymer Ed.* 5: 99-109 (1993). The reaction with sodium borohydride or sodium cyanoborohydride results in the reduction of aldehydes to alcohols. Additionally, periodate can modify the vicinal hydroxyl groups in hyaluronic acid to aldehyde groups. Free amino groups in collagen then can form Schiff bases with these aldehyde groups. These Schiff bases can also be reduced by reaction with sodium borohydride or sodium cyanoborohydride to more stable amides.

As another alternative, when cross-linking is performed with glutaraldehyde, a calcification inhibitor can be used. Such calcification inhibitors are described in U.S. Pat. No. 4,378,224 to Nimni et al., incorporated herein by this reference. Additionally, bridging agents, such as diamines, can be further included as described in U.S. Pat. No. 4,378,224 to Nimni et al. Suitable diamines are aliphatic diamines, including, but not limited to, hexanediamine.

Typically, compositions according to the present invention are formulated for injection. Typically, the route of injection is subcutaneous or intradermal, although other routes of injection are possible. Formulations suitable for injection are well known in the art, and can, for example, include sterile aqueous solutions and/or dispersions; formulations including sesame oil, peanut oil, synthetic fatty acid esters such as ethyl oleate, triglycerides, and/or aqueous propylene glycol; and/or sterile powders for the extemporaneous preparation of sterile injectable solutions and/or dispersions. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions or suspensions where appropriate. In all cases the form must be sterile and/or must be fluid to the extent that the solution will pass readily through a syringe and needle of suitable diameter for administration. It must be stable under the conditions of manufacture and storage and must be preserved against the contaminating action of microorganisms, such as bacteria or fungi. Other additives, excipients, and preservatives well known in the art can be used.

Accordingly, one aspect of the invention is an injectable composition having dermal filling and tissue expanding activity comprising:

(1) a quantity of elastin sufficient to bring about dermal filling and tissue expansion when injected into a subject in need of dermal filling and tissue expansion; and (2) a pharmaceutically acceptable carrier.

Typically, the elastin is selected from the group consisting of non-human mammalian elastin and human elastin. If the elastin is non-human mammalian elastin, it is typically porcine elastin.

The pharmaceutically acceptable carrier can comprise gelatin. It can further comprise phosphate buffered saline or other excipients; other excipients such as glucose or maltose have been described and are known in the art. In another alternative, the pharmaceutically acceptable carrier can comprise carboxymethylcellulose.

In one preferred alternative, the composition further comprises a rapid-acting local anesthetic. The rapid-acting local anesthetic can be selected from the group consisting of lidocaine, benzocaine, tetracaine, bupivacaine, cocaine, etidocaine, flecainide, mepivacaine, pramoxine, prilocaine, procaine, chloroprocaine, oxyprocaine, proparacaine, ropivacaine, dyclonine, dibucaine, propoxycaine, chloroxylenol, cinchocaine, dexivacaine, diamocaine, hexylcaine, levobupivacaine, propoxycaine, pyrrocaine, risocaine, rodocaine, and pharmaceutically acceptable derivatives and bioisosteres thereof. Typically, the rapid-acting local anesthetic is lidocaine.

The elastin can be cross-linked with a cross-linking agent, as described above. The cross-linking agent can be selected from the group consisting of a proanthocyanidin, a bifunctional epoxide, a carbodiimide, and glutaraldehyde. If the cross-linking agent is a bifunctional epoxide, it is typically 1,4-butanediol diglycidyl ether. If the cross-linking agent is a carbodiimide, the carbodiimide is typically selected from the group consisting of 1-ethyl-3-(3-dimethylaminopropyl) carbodiimide hydrochloride (EDC), dicyclohexylcarbodiimide (DCC), 1-ethyl-3-(4-azonia-4,4-dimethylpentyl) carbodiimide iodide (EAC); 1-cyclohexyl-3-(2-morpholinyl-(4)-ethyl-carbodiimide metho-p-toluenesulfonate (CMC), and N-benzyl-N'-3-dimethylaminopropyl-carbodiimide hydrochloride (BDC). Preferably, the carbodiimide is 1-ethyl-3-(3-dimethylaminopropyl) carbodiimide hydrochloride (EDC).

In one preferred alternative, the elastin is cross-linked with a glycosaminoglycan. The glycosaminoglycan can be selected from the group consisting of hyaluronic acid, chondroitin sulfate, pentosan polysulfate, dermatan sulfates, heparin, heparan sulfates, and keratan sulfates. Typically, the glycosaminoglycan is hyaluronic acid. Suitable cross-linking agents are as described above. When the glycosaminoglycan is hyaluronic acid, the hyaluronic acid can be obtained from rooster combs or can be synthesized by bacteria.

In another preferred alternative, the composition further comprises collagen. The collagen can be native or denatured collagen obtained from skin, tendon, ligament, pericardium, dural membrane, small intestine mucosa or bone. The collagen can be used in soluble form, fibrillar form, a form of an insoluble slurry, or hydrogel form. The collagen can be human Type I collagen. The human Type I collagen can be obtained from demineralized bone matrix (DBM). Alternatively, the collagen can be collagen from porcine tendon. The collagen can be cross-linked intramolecularly. Suitable cross-linking agents are described above. Alternatively, the collagen can be cross-linked to the elastin, or the collagen can be cross-linked to a glycosaminoglycan such as, but not limited to, hyaluronic acid, which can also be included in the composition in that alternative.

The elastin can be obtained from human or animal ligaments or arteries. Typically, the elastin is purified from non-elastineous proteins and proteoglycans. Typically, the elastin is cryofractured into a fine particle. Preferably, the size of the fine particle is from about 50 μm to about 210 μm. Typically, the elastin concentration is from about 20 mg/mL to about 300 mg/mL; preferably, the elastin concentration is from about 20 mg/mL to about 100 mg/mL.

In one alternative of this aspect of the invention, the composition further comprises collagen and a glycosaminoglycan such as, but not limited to, hyaluronic acid, and wherein one or more of the elastin, the collagen, and the glycosaminoglycan are cross-linked, either intramolecularly or intermolecularly. Suitable cross-linking agents are described above.

Another aspect of the invention is a method of dermal filling and tissue expansion comprising the step of injecting a quantity of this embodiment of a composition according to the present invention as described above sufficient to induce dermal filling and tissue expansion to a patient in need thereof. In this method, the dosage, the frequency of the dosage, and the route of injection can be chosen by a skilled clinician taking into account such factors as the condition of the skin of the patient, the specific wrinkles, folds, or other imperfections visible, the degree of improvement desired, the sex, age, weight, and general physical condition of the patient, the presence of other preexisting conditions affecting the skin or the connective tissue, the possibility of side effects or hypersensitivity caused by any ingredient of the composition, and the existence of conditions, such as liver or kidney conditions, that will affect the pharmacokinetics of any ingredient of the composition.

Another aspect of the present invention is an injectable composition having dermal filling and tissue expanding activity comprising:

(1) an insoluble collagen suspension in a quantity sufficient to bring about dermal filling and tissue expansion when injected into a subject in need of dermal filling and tissue expansion; and (2) a pharmaceutically acceptable carrier.

Typically, in this composition, the concentration of collagen is from about 20 mg/mL to about 100 mg/mL. Typically, in this composition, the collagen is cross-linked with a cross-linking agent, as described above.

Typically, in this composition, the pharmaceutically acceptable carrier is gelatin.

In this aspect of the invention, the composition can further comprise elastin. In one preferred alternative when the composition comprises elastin, the composition comprises 75 mg of elastin particles and 25 mg of insoluble collagen per 1.0 mL of pharmaceutically acceptable carrier. In this alternative, the pharmaceutically acceptable carrier can be gelatin.

In this aspect of the invention, the collagen can be partially denatured into gelatin to aid in maintaining the components in suspension and in facilitating the injection of the mixture through a narrow gauge needle.

Other components can be included. For example, the composition can further comprise a growth factor. The growth factor can be one or more of the following: an interleukin; a bone morphogenetic protein (BMP); brain-derived neurotrophic factor (BDNF); transforming growth factor α(TGF α); transforming growth factor $\beta_1$ (TGF $\beta_1$); transforming growth factor $\beta_2$ (TGF $\beta_2$); acidic fibroblast growth factor (aFGF); basic fibroblast growth factor (bFGF); granulocyte colony-stimulating factor (G-CSF); glial cell line-derived growth factor (GDNF); granulocyte/macrophage colony-stimulating factor (GM-CSF); growth hormone; haemoinfiltrate CC chemokine 1 (HCC-1); insulin-like growth factor I (IGF I); insulin-like growth factor II (IGF II); macrophage colony-stimulating factor (M-CSF); and stem cell factor (SCF). The use of other growth factors is possible.

These growth factors are described in general in K. A. Fitzgerald et al., The Cytokine Facts Book (2d ed., Academic Press, San Diego, 2001). Specifically, the interleukins include IL-1, IL-2, IL-3, IL-4, IL-5, IL-6, IL-7, IL-8, IL-9, IL-10, IL-11, IL12, IL-13, IL-14, IL-15, IL-16, IL-17, and IL-18. IL-1 exists in two forms, IL-1α and IL-1β. IL-1α has 159 amino acids in the mature form in human and 156 in mouse; IL-1β has 153 amino acids in the mature form in human and 159 in mouse. IL-2 has 133 amino acids in the mature form in human and 149 in mouse. IL-3 has 133 amino acids in the mature form in human and 140 in mouse. IL-4 has 129 amino acids in the mature form in human and 120 in mouse. IL-5 has 115 amino acids in the mature form in human and 113 amino in mouse. IL-6 has 183 amino acids in the mature form in human and 187 in mouse. IL-7 has 152 amino acids in the mature form in human and 129 in mouse. IL-8 has 99 amino acids in the mature form in human. IL-9 has 126 amino acids in the mature form in human and 126 in mouse. IL-10 has 160 amino acids in the mature form in human and 160 in mouse. IL-11 has 178 amino acids in the mature form in human and 178 in mouse. IL-12 has 115 amino acids in the mature form in human and 113 amino in mouse. IL-13 has 112 amino acids in the mature form in human and 113 amino in mouse. IL-114 has 483 amino acids in the mature form in human. IL-15 has 113 amino acids in the mature form in human and 114 in mouse. IL-16 has 115 amino acids in the mature form in human and 113 amino in mouse. IL-17 has 132 amino acids in the mature form in human and 133 amino in mouse. IL-18 has 522 amino acids in the mature form in human and 519 in mouse.

The BMPs are described in further detail in the following publications: (1) F. P. Luyten et al., "Purification and Partial Amino Acid Sequence of Osteogenin, a Protein Initiating Bone Differentiation," J. Biol. Chem. 264: 13377-13380 (1989); (2) E. Özkaynak et al., "Murine Osteogenic Protein (OP-1): High Levels of mRNA in Kidney," Biochem. Biophys. Res. Commun. 179: 116-123 (1991); (3) R. M. Harland et al., "The Transforming Growth Factor β Family and Induction of the Vertebrate Mesoderm: Bone Morphogenetic Proteins are Ventral Inducers," Proc. Natl. Acad. Sci. USA 91: 10243-10246 (1994); (4) S. K. Maiti & G. R. Singh, "Bone Morphogenetic Proteins-Novel Regulators of Bone Formation," Ind. J. Exp. Biol. 36: 237-244 (1998); (5) J. M. Wozney et al., "Novel Regulators of Bone Formation: Molecular Clones and Activities," Science 242: 1528-1534 (1988); (6) D. M. Kingsley et al., "What Do BMPs Do in Mammals? Clues from the Mouse Short-Ear Mutation," Trends Genet. 10: 16-21 (1994); (7) C. Scheufler et al., "Crystal Structure of Human Bone Morphogenetic Protein-2 at 2.7 Å Resolution," J. Mol. Biol. 287: 103-115 (1999); (8) J. Q. Feng et al., "Structure and Sequence of Mouse Bone Morphogenetic Protein-2 Gene (BMP-2): Comparison of the Structures and Promoter Regions of BMP-2 and BMP-4 Genes," Biochim. Biophys. Acta 1218: 221-224 (1994); (9) N. Ghosh-Choudhury et al., "Expression of the BMP 2 Gene During Bone Cell Differentiation," Crit. Rev. Eukaryot. Gene Expr. 4: 345-355 (1994); (10) B. L. Rosenzweig et al., "Cloning and Characterization of a Human Type II Receptor for Bone Morphogenetic Proteins," Proc. Natl. Acad. Sci. USA 92: 7632-7636; (11) L. J. Jonk et al., "Identification and Functional Characterization of a Smad Binding Element (SBE) in the JunB Promoter That Acts as a Transforming Growth Factor-β, Activin, and Bone-Morphogenetic-Protein-Inducible Enhancer," J. Biol. Chem. 273: 21145-21152 (1998); and (12) M. Kawabata et al., "Signal Transduction by Bone Morphogenetic Proteins," Cytokine Growth Factor Rev. 9: 49-61 (1998). The BMPs represent a family of proteins that initiate, promote, and maintain cartilage and bone morphogenesis, differentiation and regeneration in both the developing embryo and the adult. There are more than 30 known BMPs, of which 15 are found in mammals. BMPs belong to the transforming growth factor β (TGFβ) superfamily, which includes TGFβs, activins/inhibins, Mullerian-inhibiting substance (MIS) and glial cell line-derived neurotrophic factor.

Comparison and alignment of the amino acid sequences of BMPs reveal that BMPs, except for BMP-1, share a common structural motif that is distinct from the structure of BMP-1. These BMPs include BMP-2, BMP-3, BMP-3b, BMP4, BMP-5, BMP-6, BMP-7, BMP-8, BMP-8B, GDF-3, GDF-5, GDF-6, GDF-7, GDF-8, GDF9, GDF-10, and nodal. In this specification, the term "BMP," without further qualification, is to be taken to include BMP-1; the term "BMP sharing a common structural motif" is to be taken to include BMPs other than BMP-1 and exclude BMP-1. These BMPs sharing a common structural motif are disulfide-linked dimeric proteins. BMP-1 is not properly a BMP family member; rather it is a procollagen C proteinase related to Drosophila tolloid and which is postulated to regulate BMP activity through proteolysis of BMP antagonists/binding proteins.

BDNF has 119 amino acids in the mature form in both human and, mouse. It has 70% β-sheet and is expressed as a tightly associated homodimer.

TGF α has 50 amino acids in the mature form in both human and rat. It is a small integral membrane protein.

TGF $β_1$ has 112 amino acids in the mature form in humans; there is greater than 98% homology between the functional regions of human and mouse molecules.

TGF $β_2$ also has 112 amino acids in the mature form in humans; there is again greater than 98% homology between the functional regions of human and mouse molecules.

The growth factor aFGF has 155 amino acids in the mature form in humans and in mice.

The growth factor bFGF has 155 amino acids in the mature form in humans and 154 amino acids in the mature form in mice. The growth factor bFGF is composed entirely of a β-sheet structure with a 3-fold repeat of a four-stranded antiparallel β-meander that forms a barrel-like structure with three loops.

G-CSF has 177 or 174 amino acids in the mature form in humans and 178 amino acids in the mature form in mice. The 177-amino-acid and 174-amino-acid forms in humans are alternatively spliced variants. G-CSF forms a four α-helical bundle structure.

GDNF has 134 amino acids in the mature form in humans and mice.

GM-CSF has 127 amino acids in the mature form in humans and 124 amino acids in the mature form in mice. The molecule comprises a two-stranded antiparallel β-sheet with an open bundle of four α-helices.

Growth hormone has 191 amino acids in the mature form in humans and 190 amino acids in the mature form in mice. The molecule forms a four α-helical bundle structure.

HCC-1 has 74 amino acids in the mature form in humans.

IGF I exists in two isoforms, IGF IA and IGF IB. Both consist of A and B domains, homologous to the A and B chains of insulin, connected by a C peptide and an eight-amino-acid extension at the C terminus termed the D domain. In humans and in mice, the IGF IA and IGF IB isoforms are both 70 amino acids in length in the mature form. IGF I has a three-dimensional structure similar to insulin.

IGF II has 67 amino acids in the mature form in both humans and mice. It also consists of A, B, C, and D domains. IGF II also has a three-dimensional structure similar to insulin.

M-CSF exists in three mature forms in humans, with 522, 406, and 224 amino acids respectively. In mice, the mature form of M-CSF has 519 amino acids. At least a portion of the structure of M-CSF comprises two bundles of four α-helices laid end to end.

SCF has 248 or 220 amino acids in the mature form in both humans and mice, existing in long and short membrane-bound forms after removal of the predicted signal peptide. The molecule exists as a noncovalently linked homodimer that contains extensive α-helical and β-pleated sheets.

These growth factors can exist in multiple forms, such as: (1) splicing variants produced from mRNAs generated by spicing from alternative sites; (2) variants produced by proteolysis, such as the cleavage of signal peptides or propeptides; (3) variants produced by the presence or lack of glycosylation, typically N-linked glycosylation; (4) naturally-occurring isoforms; (5) naturally-occurring mutations or allelic variants; and (6) artificial variants produced by genetic engineering in which one or more amino acids in the primary sequence are altered by techniques such as site-specific mutagenesis; such artificial variants are frequently designated muteins. In general, these multiple forms are within the scope of the present invention when they exist or can be produced for a particular growth factor.

Another aspect of the invention is a method of dermal filling and tissue expansion comprising the step of injecting a quantity of this embodiment of a composition according to the present invention as described above sufficient to induce dermal filling and tissue expansion to a patient in need thereof. In this method, the dosage, the frequency of the dosage, and the route of injection can be chosen by a skilled clinician taking into account the factors described above.

Yet another aspect of the present invention is a method for augmenting the volume area of dermal tissue at sites where wrinkles and other tissue imperfections have caused visible changes associated with loss or rearrangement of the subcutaneous collagen network comprising the step of: providing an effective amount of a composition, which can be injected locally, and which consists of a mixture of macromolecules which are native constituents of the skin, the mixture comprising collagen, elastin and, optionally, a glycosaminoglycan, such as, but not limited to, hyaluronic acid, which are held together by covalent, ionic or hydrogen bonds, and which include natural materials which have been demonstrated to increase the natural synthesis of these molecules by cells which reside in the dermis. In this method, the collagen can be native or denatured collagen obtained from skin, tendon, ligament, pericardium, dural membrane, small intestine mucosa or bone. The collagen can be used in soluble form, fibrillar form, a form of an insoluble slurry, or hydrogel form. The collagen can be cross-linked intramolecularly. Alternatively, the collagen can be cross-linked to the elastin or to the glycosaminoglycan, such as, but not limited to, hyaluronic acid. The collagen can be insoluble collagen; when the collagen is insoluble collagen, the concentration of insoluble collagen is typically from about 20 mg/mL to about 100 mg/mL.

The elastin used can be obtained from human or animal ligaments or arteries. The elastin is typically purified from non-elastineous proteins and proteoglycans. The elastin is typically cryofractured into a fine particle. Typically, the size of the fine particle is from about 50 μm to about 210 μm.

In this method, the injectable composition used typically comprises gelatin.

In this method, typically, the elastin concentration is from about 20 mg/mL to about 100 mg/mL.

In this method, when the glycosaminoglycan is hyaluronic acid, the hyaluronic acid used can be obtained from rooster combs or is synthesized by bacteria.

In this method, at least one of the collagen, the elastin, and the glycosaminoglycan, such as, but not limited to, hyaluronic acid, can be cross-linked, either intramolecularly or intermolecularly, by use of a cross-linking agent. The cross-linking agent can be selected from the group consisting of proanthocyanidin, a bifunctional epoxide, a carbodiimide, and glutaraldehyde, as described above. As another alternative, additional stabilizing cross-links can be introduced into at least one of the collagen, the elastin, and the glycosaminoglycan, by use of a water-soluble carbodiimide, a periodate, or an epoxide. Specifically, proanthocyanidin as a cross-linker acts as a protector of elastin against ultraviolet degradation. Additionally, proanthocyanidin combined with a gelatin or collagen-hyaluronic acid matrix can inhibit matrix degradation and contraction by fibroblasts as described in L. L. H. Huang-Lee & M. E. Nimni, "Fibroblast Contraction of Collagen Matrices With and Without Covalently Bound Hyaluronan," *J. Biomater. Sci. Polymer Ed.* 5: 99-109 (1993). Additionally, when periodate is used as a cross-linker, the aldehydes formed can then be stabilized further by reaction with sodium borohydride to give rise to more permanent cross-links, such as collagen-hyaluronic acid cross-links, as shown in FIG. 5 of L. L. H. Huang-Lee & M. E. Nimni, "Fibroblast Contraction of Collagen Matrices With and Without Covalently Bound Hyaluronan," *J. Biomater. Sci. Polymer Ed.* 5: 99-109 (1993). The reaction with sodium borohydride results in the reduction of the aldehyde groups to alcohols. As another alternative, when cross-linking is performed with glutaraldehyde, a calcification inhibitor can be used. Such calcification inhibitors are described in U.S. Pat. No. 4,378,224 to Nimni et al., incorporated herein by this reference. Additionally, bridging agents, such as diamines, can be further included as described in U.S. Pat. No. 4,378,224 to Nimni et al. Suitable diamines are aliphatic diamines, including, but not limited to, hexanediamine.

Typically, in this method, the mixture is dried, pulverized into small particles, suspended in a physiological compatible solution, and injected subcutaneously or intradermally to humans.

The following references are relevant to the understanding of the present invention, although Applicants do not state that such references constitute relevant prior art: (1) Injectable collagen for tissue augmentation, D G Wallace et al., In Collagen, Vol III, Editor M. E. Nimni, CRC Press (1988), pp 117-144; (2) U.S. Pat. No. 4,233,360 to Luck et al.; and (3) U.S. Pat. No. 4,424,208 to Wallace et al.

Additionally, the following patents are relevant to the understanding of the present invention and can provide alternative methods and reagents for practicing the invention, although Applicants do not state that such references constitute relevant prior art: U.S. Pat. No. 4,557,664 to Chu; U.S. Pat. No. 4,582,640 to Smestad et al.; U.S. Pat. No. 4,760,131 to Sundsmo et al.; U.S. Pat. No. 4,774,227 to Piez et al.; U.S. Pat. No. 4,789,663 to Wallace et al.; U.S. Pat. No. 4,803,075 to Wallace et al.; U.S. Pat. No. 4,863,732 to Nathan et al.; U.S. Pat. No. 4,950,483 to Ksander et al., U.S. Pat. No. 5,110,604 to Chu et al.; U.S. Pat. No. 5,162,430 to Rhee et al.; U.S. Pat. No. 5,219,576 to Chu et al.; U.S. Pat. No. 5,304,595 to Rhee et al.; U.S. Pat. No. 5,328,955 to Rhee et al.; U.S. Pat. No. 5,413,791 to Rhee et al.; U.S. Pat. No. 5,446,091 to Rhee et al.; U.S. Pat. No. 5,470,911 to Rhee et al.; U.S. Pat. No. 5,475,052 to Rhee et al.; U.S. Pat. No. 5,476,666 to Rhee et al.; U.S. Pat. No. 5,510,418 to Rhee et al.; U.S. Pat. No. 5,510,418; U.S. Pat. No. 5,523,348 to Rhee et al.; U.S. Pat. No. 5,527,856 to Rhee et al.; U.S. Pat. No. 5,550,187 to Rhee et al.; and U.S. Pat. No. 5,614,587 to Rhee et al.

Applicants believe that the novelty of the present invention resides in the following: (1) the combination of all 3 ingredients, collagen, elastin and HA; (2) the use of the most insoluble form of tissue collagen, namely bone collagen, in one of our preferred embodiments; (3) cross-linking with a proanthocyanidin, a natural bioflavonoid; (4) use of this same bioflavonoid to enhance new collagen synthesis (as shown in our paper of 2003 (Han B Nimni et al. Proanthocyanidin: a natural cross-linking reagent for stabilizing collagen matrices, J. Biomed. Mater. Res 65 (1): 118124) and to protect elastin against UV damage; (5) the suspension of particulate elastin in a mixture of collagen-gelatin-hyaluronic acid cross-linked with proanthocyanidin (with or without further enhancement of cross-links by carbodiimide or epoxide reagents); (6) the long term persistence of this mixture below the dermal epidermal junction; (7) the negligible or minimal immune reactivity of this composite; (8) the preferred embodiments use pig tendon, which has significant identity to human collagen, and also use demineralized bone matrix from various sources, including, but not limited to, human bone obtained from bone banks. The use of a proanthocyanidin to cross-link, stabilize, or coat elastin in a microparticle suspension is highly preferred in order to prevent its biodegradation. If not cross-linked, stabilized, or coated, elastin degrades rapidly, as determined by an in vitro enzyme degradation test.

The invention is illustrated by the following examples. These examples are for illustrative purposes only, and are not intended to limit the invention.

EXAMPLES

Example 1

Elastin Preparation

Porcine aorta roots weighing about 300 g was soaked in PBS overnight at 4° C. for 24 hours with 3 changes of solution to remove adherent blood and other water soluble proteins. After wash, aorta roots were soaked in 1000 mL of 0.4 M guanidine HCl and heated at 100° C. for 45 min. After being rinsed with water, the materials were transferred into 500 mL of 0.1 N NaOH and heated at 50° C. for 45 min. After subsequent washing, tissues were air dried and ready for cryofracture.

Alternatively, after initial washing with PBS, aorta roots were soaked in 0.5 N NaOH and heated at 50° C. for 45 min. Samples were washed and then sonicated in water for 30 min. Tissues were heated at 100° C. in water for 30 min followed by water washing (three times). Elastin was air-dried in fume hood followed by cyrofracture (pulverization) in liquid nitrogen (SPEX Freezer Mill). Particles were sieved and particle sized from 50-210 µm were collected.

Example 2

Collagen Purification

After removing attached tissues, porcine tendon was washed with PBS at 4° C. for 12 hours with three changes of solution. After tissue was sectioned into fine slices, tissues were delipidated with chloroform/methanol overnight at 4° C. Tissues were then digested in 0.5 M acetic acid with 0.5 mg/ml pepsin (Sigma) for 48 hrs at 4° C. to remove telopeptide. The supernatants were collected after centrifugation. Collagen was precipitated with 2.5 M NaCl. The precipitated collagen w then dissolved in 1 M NaCl, 0.05 M Tris, pH 7.4, then sequentially dissolved and precipitated with 1.8 M NaCl and 2.5 M NaCl to produce pure Type I collagen. Collagen was dissolved into 0.5 M acetic acid and further dialyzed against 0.01 N HCl. Purified collagen was stored at 4° C.

To obtain denatured collagen, collagen was neutralized with 0.1 N NaOH to pH 7.4. Collagen solution was autoclaved at 127° C. for 30 minutes to denature the collagen.

Alternatively, insoluble bone collagen was used. Human DBM (demineralized bone matrix) obtained from tissue bank with a particle size from 50-210 μm was also used as insoluble collagen source. DBM was inactivated with 6M Guanidine-HCl for 24 hr at 4° C. The material after processing is sterile and devoid of any viral pathogens and antigenic proteins for the respective species for which it will be utilized.

Example 3

Injectable Formulations

The following injectable formulations were prepared:

Formulation I comprises elastin cross-linked with proanthocyanidin (PA) with gelatin as a carrier. Elastin was further cross-linked with 0.05% proanthocyanidin solution overnight, after washing with PBS three times. 250 mg elastin particles were suspended in 3 ml of 10% porcine tendon gelatin solution.

Formulation II comprises elastin cross-linked with bifunctional epoxide with gelatin as a carrier. Elastin was added into 4% EGDA, 4 M NaCl in 0.5 N NaOH for 2 h at 37° C., and then transferred into PBS solution and washed for 2 h. 250 mg elastin particles were suspended in 3 ml of 10% porcine tendon gelatin solution.

Formulation III comprises elastin cross-linked with hyaluronic acid (HA) with 1-ethyl-3-(3-dimethylaminopropyl) carbodiimide hydrochloride (EDC) and gelatin as a carrier. Cross-linked HA was prepared by first adding 29.72 mg EDC and 53.6 mg NHS in 10 mL deionized water. 100 mg HA (rooster comb) was added to the EDC/NHS solution and stirred for 2 hours. Elastin was added to the cross-linked HA solution overnight. The particles were washed with PBS three times. Elastin-HA particles were suspended in porcine tendon gelatin solution for injection.

Formulation IV comprises a suspension of elastin, insoluble collagen, and gelatin. 75 mg of elastin particles and 25 mg of insoluble bone collagen were mixed and suspended in 1.0 mL of gelatin solution.

Formulation V comprises insoluble bone collagen cross-linked with hyaluronic acid and gelatin as a carrier, with or without elastin. In this formulation, in the activated HA EDC/NHS solution described above, insoluble bone collagen particles were stirred overnight. Insoluble bone collagen particles with or without 25 mg of elastin were then suspended in gelatin solution for injection.

Example 4

Animal Tests

Fisher 344 rats were anesthetized with intraperitoneal injections of xylazine (10 mg/kg) and ketamine (50 mg/kg). Skin was shaved on the dorsal site and 23-27 G needle was used to inject materials into subcutaneous sites. Each animal received 4 injections. After 2 weeks or 4 weeks, animals were sacrificed and injected samples and surrounding tissues were evaluated macroscopically and microscopically after histological processing.

The results are shown in FIGS. 1-11, below. It can be clearly seen that the mixtures were in general well tolerated, with differences in response and persistence of the implants depending on the ingredients and modalities of handling. In general, elastin that was not cross-linked undergoes partial degradation. When cross-linked with epoxide, it is tolerated extremely well. In general, results where cross-linking was performed with proanthocyanidin were similar, with increased persistence and a variable degree of inflammatory response depending on the concentration of proanthocyanidin. The moderate inflammatory response is viewed as an advantage, as it dissipates after 4 weeks, but results in an enhanced deposition of collagen in the area of the implant.

This deposition of collagen, which seems to correlate with the rate of resorption of the implant, extends the space filling effect of the implant, thus contributing to the efficacy of the procedure. It is expected that this biological response will correlate with the long term elimination of wrinkles and other undesirable skin surface characteristics.

FIG. 1 shows the results with elastin (without cross-linking) with gelatin as a carrier after four weeks (×200 magnification for FIGS. 1-6).

Figure 2:
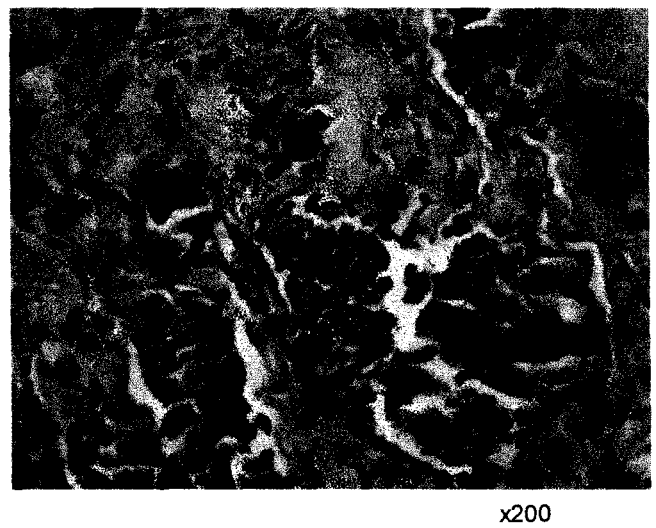
FIG. 2 is a photomicrograph at ×200 magnification showing the results with elastin cross-linked with bifunctional epoxide with gelatin as a carrier in rats treated with the composition (Example 4).

FIG. 2 shows the results with elastin cross-linked with bifunctional epoxide with gelatin as a carrier.

Figure 3:
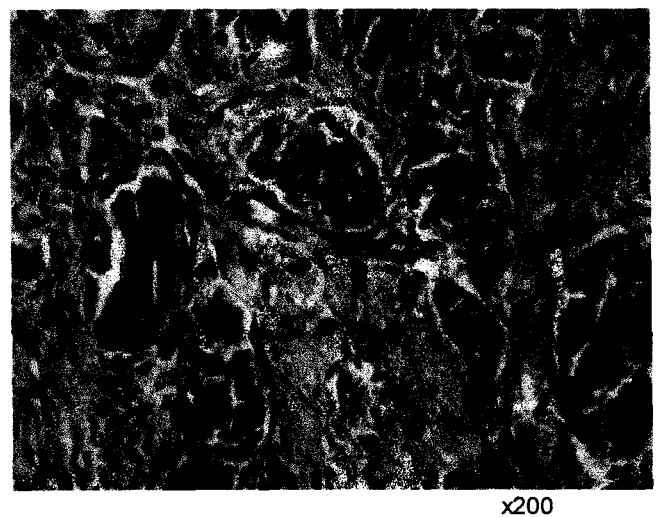
FIG. 3 is a photomicrograph at ×200 magnification showing the results with elastin cross-linked with proanthocyanidin with gelatin as a carrier in rats treated with the composition (Example 4).

FIG. 3 shows the results with elastin cross-linked with proanthocyanidin with gelatin as a carrier.

Figure 4:
FIG. 4 is a photomicrograph at ×200 magnification showing the results with hyaluronic acid cross-linked to a DBM surface, injected with a 23 G needle in rats treated with the composition (Example 4).

FIG. 4 shows the results with hyaluronic acid cross-linked to a DBM surface, injected with a 23 G needle.

FIG. 5 shows the results with hyaluronic acid cross-linked to a DBM surface, injected with a 23 G needle.

Figure 6:
FIG. 6 is a photomicrograph at ×200 magnification showing the results with DBM cross-linked to hyaluronic acid in rats treated with the composition (Example 4).

FIG. 6 shows the results with DBM cross-linked to hyaluronic acid.

FIG. 7 shows the results of elastin cross-linked with proanthocyanidin (PA), epoxide (EP), or hyaluronic acid (HA) with subcutaneous implantation in rats for four weeks. The results are shown in FIG. 7 in the following arrangement. The leftmost column is elastin cross-linked with PA, the center column is elastin cross-linked with EP, and the rightmost column is EP cross-linked with HA. The top row shows staining with hematoxylin-eosin (H & E); the bottom row shows staining with Verhoeff-Van Gieson stain (VVG), which stains elastic fibers (in black) and collagen (in red). In the results of FIG. 7, the elastin groups showed mild foreign tissue responses in all groups. They showed strong tissue regeneration around implants. The overall degradation rates in elastin groups were low. PA and HA appear to induce more infiltration of fibroblast cells into elastin particles. Regeneration is obvious surrounding the elastin particles and into the fiber spaces. In FIG. 7, elastin-PA and elastin-HA are shown at 200× magnification; elastin-EP is shown at 400× magnification. In these experiments, both intermolecular and intramolecular cross-links were formed by the proanthocyanidin or epoxide when these reagents were used to cross-link elastin. Glutaraldehyde cannot be used to cross-link elastin because elastin lacks free $\epsilon$-$NH_2$ groups for such cross-linking by reaction with a carbonyl group. If hyaluronic acid was used, carbodiimide was used as the cross-linking reagent to cross-link hyaluronic acid to elastin, forming intermolecular cross-links. In these and the following experiments, the elastin concentration was from 70 mg/ml to 320 mg/ml. In one embodiment, 78 mg/ml elastin in 5% gelatin/PBS was used as carrier. Alternatively, carboxymethylcellulose was used as a carrier.

FIG. 8 shows that the implants kept their injected shapes throughout the implantation period. Few or no contracture bands are seen in FIG. 8 (100× magnification, 4-week implantation, panels A-C). In FIG. 8, and other similar figures, a blue-black color was seen as the result of specific staining of elastin by the Verhoeff-Van Gieson staining method. Using the Verhoeff-Van Gieson staining method, staining was performed as follows: After slides were deparaffinized and hydrated with distilled water, slides were first stained 15 min in Verhoeff's Iron Hematoxylin. Excess stain was rinsed off in tap water for 20 minutes. Solution of 2% aqueous ferric chloride was used to differentiate elastic fibers by staining these fibers black. Then slides were placed in 5% sodium thiosulfate for 1-2 minutes and counterstained in Van Gieson solution for 1 minute. Elastic fibers were stained intensely blue to black. Collagen was stained pink to red and other tissue elements were stained yellow. In FIG. 8, the smaller panels (B and C) were with 40× magnification. They are different sections from the same type of implants, but not the same tissue. These panels show that the injected samples are stay at the injection place and keep their original shapes.

Figure 9:
FIG. 9 shows that fibrous tissues formed surrounding the elastin particles (solid arrow) and fibroblasts migrated into elastin fibers to regenerate fibrous tissues (dotted arrows). Magnification in FIG. 9 was 200×.

FIG. 9 shows that fibrous tissues formed surrounding the elastin particles (solid arrow) and fibroblasts migrated into elastin fibers to regenerate fibrous tissues (dotted arrows). Magnification in FIG. 9 was 200×.

Figure 10A:
FIG. 10A shows insoluble collagen plus elastin implanted subcutaneously in rats for 8 weeks.
Figure 10B:
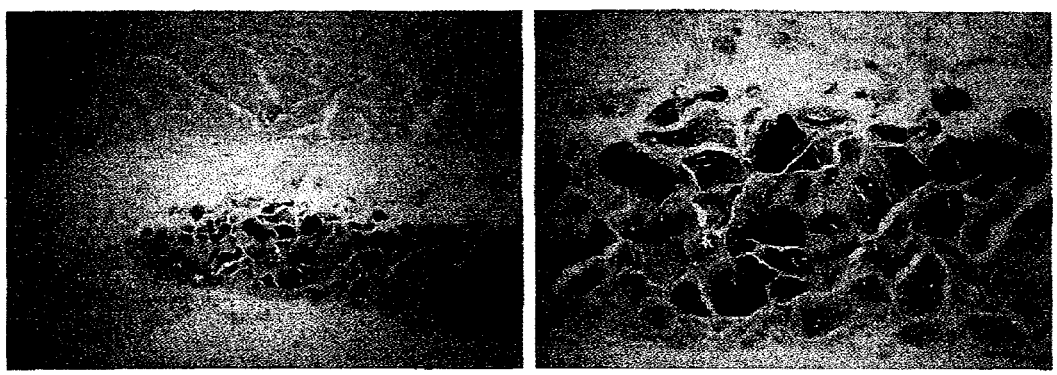
FIG. 10B shows elastin implanted subcutaneously in rats for 6 weeks (left and right panels).
Figure 10C:
FIG. 10C shows elastin cross-linked with proanthocyanidin implanted intracutaneously in rats for 6 weeks (left and right panels).

FIG. 10 shows the results of implantation of insoluble collagen together with elastin, elastin cross-linked with proanthocyanidin, or elastin alone, using different implantation times and routes of implantation. FIG. 10A shows insoluble collagen plus elastin implanted subcutaneously in rats for 8 weeks. FIG. 10B shows elastin implanted subcutaneously in rats for 6 weeks (left and right panels). FIG. 10C shows elastin cross-linked with proanthocyanidin implanted intracutaneously in rats for 6 weeks (left and right panels). FIG. 10D shows elastin cross-linked with hyaluronic acid implanted intracutaneously in rats for 6 weeks (left and right panels).

FIG. 11 shows the results with mixtures of collagen and elastin. FIG. 11A shows the results with 75% collagen and 25% elastin implanted subcutaneously in rats for 4 weeks. FIG. 11B shows the results with 25% collagen and 75% elastin implanted subcutaneously in rats for 4 weeks.

Cross-linking has a number of benefits. (1) It decreases material degradation. (2) It decreases the swellability of elastin or other ECM particles for better particle suspension and greater ease of injection (less clogging). (3) Proanthocyanidin is believed to increase fibroblast cellular activity; this should accelerate the regeneration process. (4) Proanthocyanidin is also an antioxidant that should quench free radicals generated by local inflammatory reactions.

In the results presented herein, cross-linking with epoxide was found to be more efficient in inhibiting material degradation. However, cross-linking to hyaluronic acid as described above was more effective in inducing cellular activity of fibroblasts.

The results presented herein also show that, when elastin is used, if the elastin particle size is above 50 μm which is greater than the size that macrophages can engulf, elastin in general is stable subcutaneously or intracutaneously. When an elastin particle surface is cross-linked with a soluble layer of collagen or hyaluronic acid, there can be several effects. First, the cross-linking can change the morphology or charge of the elastin surface, which can result in a better scaffold for regenerative cells such as fibroblasts to anchor, proliferate and deposit ECM. Secondly, it is possible that a change in the surface charged produced by cross-linking can enable the particles to be better suspended in a pharmaceutically acceptable carrier.

If insoluble collagen is used as a particle phase, cross-linking improves the persistence of the injected or implanted composition. If the collagen is from a xenogeneic source, cross-linking of the collagen also reduces immunogenicity.

Advantages of the Invention

The present invention provides improved compositions and methods for dermal expansion and tissue filling that are effective in both cosmetic and reconstructive contexts. These compositions and methods are effective, produce long-lasting results, and are well tolerated without migration of the compositions or other significant side effects. The inflammation that can occur is a physiological process that stimulates collagen production, leading to an improved result and elimination of wrinkles and other undesirable skin surface characteristics.

Compositions and methods according to the present invention possess industrial applicability for the production of a medicament for use as a dermal expander and tissue filler.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

We claim:

1. An injectable composition having dermal filling and tissue expanding activity comprising:
   (a) a quantity of elastin sufficient to bring about dermal filling and tissue expansion when injected into a subject in need of dermal filling and tissue expansion; and
   (b) a pharmaceutically acceptable carrier;
   wherein the composition possesses space filling activity owing to its elastin content; and
   wherein the composition further comprises collagen;
   wherein the collagen is cross-linked intramolecularly in vitro with a cross-linking agent.

2. The composition of claim 1 wherein the collagen is used in soluble form, fibrillar form, a form of an insoluble slurry, or hydrogel form.

3. An injectable composition having dermal filling and tissue expanding activity comprising:
   (a) a quantity of elastin sufficient to bring about dermal filling and tissue expansion when injected into a subject in need of dermal filling and tissue expansion; and
   (b) a pharmaceutically acceptable carrier;
   wherein the composition possesses space filling activity owing to its elastin content;
   wherein the composition further comprises collagen and a glycosaminoglycan, and wherein one or more of the elastin, the collagen, and the glycosaminoglycan are cross-linked, either intramolecularly or intermolecularly in vitro with a cross-linking agent, wherein the glycosaminoglycan is selected from the group consisting of hyaluronic acid, chondroitin sulfate, pentosan polysulfate, dermatan sulfates, heparin, heparan sulfates, and keratan sulfates.

4. The composition of claim 3 wherein the collagen is used in soluble form, fibrillar form, a form of an insoluble slurry, or hydrogel form.

* * * * *